(12) United States Patent
Smigel

(10) Patent No.: US 11,484,487 B1
(45) Date of Patent: Nov. 1, 2022

(54) GINGIVITIS GUM SERUM

(71) Applicant: Robell Research, Inc., New York, NY (US)

(72) Inventor: Lucia Smigel, New York, NY (US)

(73) Assignee: Robell Research, Inc., New York, NY (US)

( * ) Notice: Subject to any disclaimer, the term of this patent is extended or adjusted under 35 U.S.C. 154(b) by 0 days.

(21) Appl. No.: 16/519,484

(22) Filed: Jul. 23, 2019

Related U.S. Application Data

(60) Provisional application No. 62/701,905, filed on Jul. 23, 2018.

(51) Int. Cl.

| | |
|---|---|
| *A61K 8/67* | (2006.01) |
| *A61K 8/44* | (2006.01) |
| *A61K 8/41* | (2006.01) |
| *A61K 8/9794* | (2017.01) |
| *A61K 8/49* | (2006.01) |
| *A61K 8/65* | (2006.01) |
| *A61K 8/9717* | (2017.01) |
| *A61K 8/81* | (2006.01) |
| *A61K 8/37* | (2006.01) |
| *A61K 8/34* | (2006.01) |

(52) U.S. Cl.
CPC .............. *A61K 8/676* (2013.01); *A61K 8/347* (2013.01); *A61K 8/37* (2013.01); *A61K 8/416* (2013.01); *A61K 8/44* (2013.01); *A61K 8/4913* (2013.01); *A61K 8/4946* (2013.01); *A61K 8/4973* (2013.01); *A61K 8/65* (2013.01); *A61K 8/678* (2013.01); *A61K 8/8147* (2013.01); *A61K 8/8176* (2013.01); *A61K 8/9717* (2017.08); *A61K 8/9794* (2017.08); *A61K 2800/48* (2013.01); *A61K 2800/522* (2013.01); *A61K 2800/92* (2013.01)

(58) Field of Classification Search
CPC ........ A61K 8/676; A61K 8/4973; A61K 8/44; A61K 8/4946; A61K 8/8176; A61K 8/37; A61K 8/9717; A61K 8/347; A61K 8/4913; A61K 8/65; A61K 8/416; A61K 8/8147; A61K 8/678; A61K 8/9794; A61K 2800/48; A61K 2800/522; A61K 2800/92

See application file for complete search history.

(56) References Cited

U.S. PATENT DOCUMENTS

| | | | |
|---|---|---|---|
| 5,057,497 A | 10/1991 | Calam et al. | |
| 5,298,237 A * | 3/1994 | Fine ....................... | A61K 8/23 424/49 |
| 5,908,613 A | 6/1999 | Bozzacco | |
| 6,350,438 B1 * | 2/2002 | Witt ......................... | A61K 8/20 424/53 |
| 2007/0110683 A1 * | 5/2007 | Levine ................... | A61K 8/676 424/58 |
| 2010/0330002 A1 * | 12/2010 | Robinson ............. | A61K 38/482 424/48 |
| 2014/0134114 A1 * | 5/2014 | Krammer ................ | A61K 8/37 424/49 |
| 2017/0157013 A1 * | 6/2017 | Schaeffer-Korbylo ...................... | A61K 8/27 |

FOREIGN PATENT DOCUMENTS

| | | | | |
|---|---|---|---|---|
| DE | 3028782 A1 * | 2/1982 | ............. | A61K 33/30 |
| WO | WO-2019199861 A2 * | 10/2019 | ........... | A61K 36/185 |

\* cited by examiner

*Primary Examiner* — Snigdha Maewall
(74) *Attorney, Agent, or Firm* — Grace J. Fishel

(57) ABSTRACT

A gingivitis gum serum having a collagen building complex comprising between about 0.10 and 10.00 percent by weight of a stable Vitamin C derivative and between about 0.03 and 15.0 percent by weight of an amino acid complex primarily consisting of L-glycine, L-proline, L-lysine and mixtures thereof, a multi-mineral organo complex for healthy cell and tissue generation and an orally acceptable antimicrobial in a soft tissue delivery base for manual or vibratory application.

15 Claims, No Drawings

GINGIVITIS GUM SERUM

BACKGROUND OF THE INVENTION

Field of the Invention

The present invention is a gum serum including a collagen building complex and an antibacterial agent in a soft tissue delivery base.

Brief Description of the Prior Art

Gingivitis is a form and first stage of periodontal disease that occurs on the gingiva (gums) of the oral cavity most commonly on the soft tissue area around the tooth boarder. Biofilm and subsequently plaque and eventually tartar build up in the gum-tooth interfaces and interspatial areas. These areas are difficult to clean from tooth brushing and oral rinse. Therefore, the plaque and biofilm create inhabitable areas for bacteria that will then cause inflammation, swollenness, redness, bleeding, receding gums, irritation and pain to the soft tissue. Bodily systemic infections can also occur which may cause many serious diseases including heart disease, diabetes, *Candida albicans* yeast infections, stroke and lung disease. Ultimately, gingivitis will turn into periodontal disease which often results in tooth loss.

The common over-the-counter methods for reducing gingivitis are the use of antimicrobial containing dentifrices and antimicrobial containing oral rinses. Commonly, dentifrices and mouthwashes (e.g., oral rinses) are used for under one minute and then expelled after use. Due to lack of efficacy, these products are often labeled with statements such as, 'to help prevent gingivitis.' These products can be found in such products as Crest's ProHealth and Colgate's Total. The professional, in-dental-office market may incorporate such methods, as well. In addition, dentists may use antibiotics and surgery, such as flap surgery and physical and laser scaling of tartar and grafting. But killing bacteria and excising plaque buildup is not enough to reverse gingivitis or to prophylactically prevent its occurrence.

BRIEF SUMMARY OF THE INVENTION

The soft issue in the mouth is permeable for uptake of active ingredients. Many materials, often based on pH, solubility and molecular weight, can be absorbed through the mucous membrane into the epithelia and then epithelial capillaries. It is thus possible to administer and target chemicals directly to the gingiva in the areas where gingivitis occurs with the subject leave-on gingivitis gum serum formulated with active ingredients to stimulate collagen production, reduce inflammation and support healing in addition to containing an antibacterial agent.

Active ingredients in the gingivitis gum serum include a collagen building complex comprising a stable Vitamin C derivative and an amino acid complex primarily consisting of the amino acids glycine, proline and lysine in the "L" configuration in a soft tissue delivery base together with a multi-mineral organo complex for healthy cell and tissue generation and an antibacterial agent that kills plaque bacteria. The soft tissue delivery base includes water with one or more thickening agents to allow the composition to adhere such that it remains in place for effective delivery of the active ingredients to the target area between the teeth and the gingiva. In some embodiments, the composition may further include an anti-inflammatory agent to reduce swelling and in still further embodiments, the composition may include an antioxidant such a Vitamin E for healing support of damaged tissue.

DETAILED DESCRIPTION OF AT LEAST ONE PREFERRED EMBODIMENT OF THE INVENTION

The present invention is a gum serum includes a collagen building complex and an antibacterial agent in a soft tissue delivery base. The gum serum may be manually applied to the gum line in between the teeth and gums so that the composition fills any gaps present in between the teeth and gums. Once present within any gap, the antimicrobial agents kills any plaque bacteria present while the collagen building complex, promotes the regrowth of the gum tissue.

In the present invention the collagen building complex is a combination of a stable source of Vitamin C and an amino acid complex consisting primarily of the amino acids glycine, proline and lysine in the "L" configuration, and a multi-mineral organo complex containing calcium, magnesium and other important minerals such as zinc, boron, manganese, copper, potassium, chromium and strontium often in trace amounts. One suitable multi-mineral organo complex is found in Red algae complex. Stable Vitamin C derivatives include ascorbic acid, sodium ascorbyl phosphate, magnesium ascorbyl phosphate, asorbyl palmitate, ascorbyl glucoside, 3-gyceryl ascorbate, tetrahyexyldecyl ascorbate or the like. The collagen building complex may further include an antioxidant such as Vitamin E capable of promoting the regrowth of gum tissue. Collagen may also be included in the collagen building complex which may be sourced from natural plant and animal sources or by recombinant protein production systems including yeast, bacteria, mammalian cells, insects or plants. Aloe vera, allantoin, alpha-bisabolol, cannabinoids including cannabidiol (CBD), and other such anti-inflammatory topical and analgesic agents may also be included.

Suitable antimicrobial agents include quaternary ammonium compounds. Those useful in the present invention include, for example, those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethoylstearyl ammonium chloride, cetylpyridinium chloride, quaternized 5-amino-1, 3-bis(2-ethyl-hexyl)-5-methyl hexahydropyrimidine, benzalkonium chloride, benzethonium chloride and methyl benzethonium chloride are exemplary of typical quaternary ammonium antibacterial agents. A preferred antimicrobial is benzalkonium chloride. Certain essential oils that have anti-microbial effect may also be used, such as eucalyptus, orange, lemongrass, thyme, tea tree and peppermint. The constituents of essential oils may also be used such as thymol, eucalyptol and menthol.

The soft tissue delivery base includes water and a thickening agent such as carbomer. Carbomers control the viscosity and flow of the base and help distribute and suspend insoluble solids. They have the ability to absorb water to form a colloidal, mucilage-like consistency. A soft tissue delivery base and thickening agent may also be a poloxamer.

The delivery base may also include polyvinyl pyrrolidone as an adherent and polysorbate 20 which acts as a surfactant and emulsifier. Preservatives such as sodium benzoate, flavors such as eucalyptol oil and sensates such as methyl salicylate may also be included. The soft tissue delivery base may additionally contain a sweetener such as sucralose.

Concentration ranges for the gingivitis gum serum are:
L-Lysine 0.1-1.0 (narrow range) 0.01-5.0 (broader range)
L-Proline 0.1-1.0 (narrow range) 0.01-5.0 (broader range)
L-Glysine 0.1-1.0 (narrow range) 0.01-5.0 (broader range)

A formula for a specific gingivitis gum serum is:

| Common ingredient name | Grams/250 Grams | Percent by wt |
|---|---|---|
| Water | 162.50 | 65.00 |
| Sucralose | 0.50 | 0.20 |
| Aloe Vera | 0.25 | 0.10 |
| Allantion | 0.75 | 0.30 |
| Sodium Benzoate | 1.25 | 0.50 |
| Carbomer | 7.50 | 3.00 |
| Mixture having a pH 2-3 is formed with the above and adjusted with 20% by weight Ammonium Hydroxide and q.s. Sodium Hydroxide to pH about 6 to which is added: | 15.00 | |
| Sodium Ascorbyl Phosphate | 1.88 | 0.75 |
| Red Algae Complex | 0.25 | 0.10 |
| Collagen | 0.63 | 0.25 |
| Benzalkonium Chloride | 0.25 | 0.10 |
| L-Lysine | 0.50 | 0.20 |
| L-Proline | 0.50 | 0.20 |
| L-Glysine | 0.50 | 0.20 |
| Polyvinyl Pyrrolidone | 50.00 | 20.00 |
| Mixture is formed with the above and pH adjusted to with 10% by weight Ammonium Hydroxide and q.s. Sodium Hydroxide to pH 6.5-7.5 to which is added: | | |
| Polysorbate 20 | 1.25 | 0.50 |
| Vitamin E Acetate | 1.88 | 0.75 |
| Flavor (including Eucalyptol Oil and Methyl Salicylate | 6.25 | 2.50 |

The gingivitis gum serum described above containing the collagen building complex, antibacterial, anti-inflammatory agent and antioxidant in a soft tissue delivery base may be manually applied with a brush applicator including a brush applicator that vibrates. The gingivitis gum serum is useful in the treatment of gingivitis as well as prophylactically in preventing gingivitis. It is formulated to penetrate and be absorbed into interdental spaces, specifically the indentation between teeth and gingiva (sulcus) where the primary attack on the tissue fibers, ligaments and mucosa take place. The soft tissue delivery base is formulated such that the gingivitis gum serum has a residence time from 1 or 60 minutes, more specifically from 5 to 30 minutes. Different people, however, slough off the serum at different rates depending on saliva flow and other factors. The end point is also difficult to define as there may be some serum on the gum surfaces and still effective hours after the majority has been sloughed off.

The invention has been described with respect to suitable embodiments of the gingivitis gum serum for maintenance of healthy gingival tissue. As various changes could be made in the disclosed formulations without departing from the scope of the invention, it is intended that all matter contained in the above description shall be interpreted as illustrative and not in a limiting sense and that the variations are within the scope of the appended claims.

What is claimed:

1. A healing gingivitis gum serum and antibacterial agent comprising a collagen building complex comprising between about 0.10 and 10.00 percent by weight of a stable collagen promoting Vitamin C derivative uncomplexed with a metal ion and between about 0.03 and 15.0 percent by weight of an amino acid complex consisting of L-glycine, L-proline, L-lysine and mixtures thereof, said L-lysine reducing biofilm and said L-glycine and said L-proline being essential collagen building blocks, a multi-mineral organo complex for healthy cell and tissue generation and an orally acceptable quaternary ammonium antimicrobial agent in a soft tissue delivery base.

2. The gingivitis gum serum of claim 1 wherein the amino acids consisting of equal amounts of L-lysine, L-proline and L-glycine.

3. The gingivitis gum serum of claim 1 wherein the quaternary ammonium antimicrobial agent is benzalkonium chloride.

4. The gingivitis gum serum of claim 1 further including an anti-inflammatory agent.

5. The gingivitis gum serum of claim 1 wherein the anti-inflammatory agent is aloe vera and allantion.

6. A healing gingivitis gum serum and antibacterial agent comprising between about 0.10 and 10.00 percent by weight collagen and a collagen building complex comprising between about 0.10 and 10.00 percent by weight of a stable collagen promoting Vitamin C derivative uncomplexed with a metal ion and between about 0.30 and 3.0 percent by weight of an amino acid complex consisting of L-glycine, L-proline, L-lysine and mixtures thereof, said L-lysine reducing biofilm and said L-glycine and said L-proline being essential collagen building blocks, between about 0.01 and 10.00 percent by weight of a Red algae mineral complex for healthy cell and tissue generation, from about 0.50 to 0.10 percent by weight of an orally acceptable quaternary ammonium antimicrobial agent, and an anti-inflammatory healing agent in a soft tissue delivery base including water, a thickening agent and an adherent.

7. The gingivitis gum serum of claim 6 wherein the amino acids consist of equal amounts of L-lysine, L-proline and L-glycine.

8. The gingivitis gum serum of claim 6 wherein the quaternary ammonium antimicrobial agent is benzalkonium chloride.

9. The gingivitis gum serum of claim 6 wherein the thickening agent is carbomer and the soft tissue delivery base further includes a surfactant.

10. The gingivitis gum serum of claim 9 wherein the surfactant is polysorbate 20.

11. The gingivitis gum serum of claim 6 wherein the adherent is polyvinyl pyrrolidone.

12. The gingivitis gum serum of claim 11 wherein the soft tissue delivery base further includes methyl salicylate as a cooling sensate.

13. The gingivitis gum serum of claim 12 wherein the soft tissue delivery base further includes an antioxidant.

14. The gingivitis gum serum of claim 13 wherein the antioxidant is Vitamin E.

15. The gingivitis gum serum of claim 6 wherein the anti-inflammatory healing agent is cannabidiol.

* * * * *